United States Patent [19]
Arca et al.

[11] Patent Number: 6,060,610
[45] Date of Patent: May 9, 2000

[54] PROCESS FOR THE PREPARATION OF OLEFINIC EPOXIDES

[75] Inventors: Vittorio Arca, Chioggia; Piero Furlan, Treviso, both of Italy

[73] Assignee: Enichem S.p.A., San Donato Milanese, Italy

[21] Appl. No.: 09/253,508

[22] Filed: Feb. 22, 1999

[30] Foreign Application Priority Data

Mar. 5, 1998 [IT] Italy ................................. MI98A0441

[51] Int. Cl.[7] ................................................ C07D 301/12
[52] U.S. Cl. ............................................................ 549/531
[58] Field of Search ............................................. 549/531

[56] References Cited

U.S. PATENT DOCUMENTS 5,591,875  1/1997  Chang et al. ........................... 549/531
5,646,314  7/1997  Crocco et al. .......................... 549/531

FOREIGN PATENT DOCUMENTS 0 230 949  8/1987  European Pat. Off. .
0 712 852  5/1996  European Pat. Off. .
0 757 043  2/1997  European Pat. Off. .

*Primary Examiner*—Ba K. Trinh
*Attorney, Agent, or Firm*—Oblon, Spivak, McClelland, Maier & Neustadt, P.C.

[57] ABSTRACT

Process for the production of epoxides by reaction between at least one olefin and hydrogen peroxide, or a compound capable of producing hydrogen peroxide under the reaction conditions, in the presence of a catalyst consisting of titanium silicalite subjected to treatment with organic molecules comprising an amide group substituted on the nitrogen atom.

11 Claims, No Drawings

PROCESS FOR THE PREPARATION OF OLEFINIC EPOXIDES

The present invention relates to a process for the production of olefinic epoxides.

More specifically, the present invention relates to a process for the production of olefinic epoxides by the reaction of olefins and hydrogen peroxide, or compounds capable of producing hydrogen peroxide under the reaction conditions, in the presence of a titanium-silicalite catalyst, subjected to treatment with organic compounds containing the amide group.

Epoxides or olefinic oxides are intermediates which can be used for the preparation of a wide range of products. For example, epoxides can be used for the production of glycols, condensation polymers such as polyesters or for the preparation of intermediates useful in the synthesis of polyurethane foams, elastomers, seals, etc.

Numerous processes for the preparation of olefinic oxides are known in the art. For example, European patent EP 100.119 describes a process for the preparation of epoxides by reaction between an olefin and hydrogen peroxide, or a compound capable of producing hydrogen peroxide under the reaction conditions, in the presence of titanium-silicalite. These catalysts allow the production of epoxides with a high selectivity.

However, the acidity which characterizes these catalysts, even if modest, is sufficient to activate consecutive solvolytic reactions on the epoxide with the opening of the ring. This leads to an increase in the production costs due to the decrease in the yield to epoxide and for the separation of the by-products formed.

European patent EP 230.949 discloses a process for the preparation of epoxides from olefins and hydrogen peroxide which uses as catalyst a titanium silicalite treated, before or during the epoxidation reaction, with an agent that neutralizes the acidity of the catalyst itself. Neutralizing agents which can be used are organic derivatives of silicon of the type $XSiR_3$ (X=halogen, for example) or substances deriving from cations of group I and II, with a different basic strength, which are hydrosoluble.

In the case of treatment with organic derivatives of silicon, a great limitation is linked to their well-known reactivity which makes it necessary to effect a preventive treatment of the catalyst, as treatment carried out during the epoxidation reaction, by adding these compounds in continuous, would cause undesired reactions also with the solvents and reaction products.

There may be significant counterindications for the use of salts in the pre-treatment of the catalyst before the epoxidation reaction and/or by their continuous addition during the reaction itself, as also described in published European patent application 712.852. These relate to:
problems of hydrosolubility for some of these salts;
the necessity of having saline agents whose anions must, by hydrolysis, remain within certain pH ranges so as not to favour the opening of the epoxide with the formation of undesired by-products;
the necessity of being easily removed from the zeolite so as not to cause structural modifications or create particularly acid centres in the calcination phase generally carried out on the catalyst before its use;
the possibility of there being, as far as the plant is concerned, at the temperatures and for the residence times required on the bottoms of the columns used for the separation of the epoxide from the reaction solvent and from the by-products, accumulations of these salts inducing precipitation by saturation or the formation of bicarbonates and/or carbonates with the carbon dioxide, normally present, with the possible formation of scales which would prevent adequate temperature, thermal exchange, level and consequently residence time control, etc with related running and maintenance problems;
the fact that some of the cations described in the literature cited above have certain characteristics which may make it necessary to effect exchange pretreatment with these on the titanium silicalite to obtain effective and lasting reductions of its intrinsic acidity which cannot be obtained with simple treatment in continuous of the catalyst during an epoxidation reaction by the simple addition of the saline agent with feeding to the synthesis reactor;
the possibility that certain process waste cannot be sent for disposal by combustion because the presence of these cations may be absolutely counterproductive as it induces dispersion of the refractory material of the combustion ovens.

As can be seen, all the problems listed above can contribute, either alone or synergically, to considerably complicating the running of an epoxidation process and the services relating thereto.

The Applicant has succeeded in finding a process which overcomes all the difficulties and limitations described above thanks to a treatment of the catalyst (titanium silicalite) which provides an alternative to all those so far described in the known art.

In particular, this alternative treatment, effected on the catalyst in order to significantly reduce its intrinsic acidity, is carried out with organic molecules containing the substituted amide group (N—C=O).

The present invention therefore relates to a process for the production of epoxides by the reaction between at least one olefin and hydrogen peroxide, or a compound capable of producing hydrogen peroxide under the reaction conditions, in the presence of a catalyst consisting of titanium silicalite subjected to treatment with organic molecules comprising an amide group substituted on the nitrogen atom having the general formula:

(I)

wherein:
$R_1$ may be a hydrogen atom or an alkyl radical with from 1 to 20 carbon atoms, an aryl or alkylaryl radical, with from 6 to 20 carbon atoms, a cycloalkyl radical with from 7 to 20 carbon atoms, a heterocyclic ($C_7$–$C_{20}$) radical with one or more heteroatoms, the same or different, selected from N, O, S;
$R_2$ and $R_3$, the same or different, may be alkyl radicals with from 1 to 20 carbon atoms, aryl or alkylaryl radicals, with from 6 to 20 carbon atoms, cycloalkyl radicals with from 7 to 20 carbon atoms, heterocyclic ($C_7$–$C_{20}$) radicals with one or more heteroatoms, the same or different, selected from N, O, S;
in addition the radicals $R_1$, $R_2$ and $R_3$, may form saturated or unsaturated rings in couples, and contain halogen atoms, nitro, nitrile, sulfuric groups, and relative esters, phosphoric groups, and relative esters, carbonyl, hydroxyl, carboxyl, thiol, amine and ether groups.

Owing to the unexpected effect of these compounds, it is thus possible to obtain a significant reduction in the intrinsic acidity of the titanium silicalite, which is mainly responsible, in the epoxidation reaction, for the formation of by-products from the epoxide formed.

All the solutions proposed in the known art and used for increasing the selectivity in epoxidations with titanium silicalites are overcome with the process of the present invention. In this sense, the effectiveness is quite surprising as the compounds having general formula (I), owing to their particular characteristics, have a very weak basic nature, at times neutral, as in the case of 1-methyl-2-pyrrolidone or, in some cases, for example (N-(3-trifluoromethylphenyl)-pyrrolidone, they even have a weak acid behaviour.

In addition, the products having general formula (I) are characterized by high molecular dipoles which make them extremely soluble in a large number of solvents, or their mixtures, and therefore also in those in which the epoxidation reaction is preferably effected. Their boiling points are also very high, so that at the end of the epoxidation reaction these compounds can be easily separated from the reagent mixture. They additionally have a considerable chemical and thermal stability which prevents them from degrading in the reaction section and also in the purification section of the epoxide.

Examples of organic molecules comprising an amide group substituted on the nitrogen atom having general formula (I) are the following: N,N-dimethylformamide, N,N-diethylformamide, N,N-dipropylformamide, etc. and the corresponding mixed amides; N,N-dimethylacetamide, N,N-diethylacetamide, etc. and the corresponding mixed amides; dicyclohexylformamide, dicyclophenylformamide, dicyclohexylacetamide, dicyclophenylacetamide; N-methylpyrrolidone, N-ethylpyrrolidone, N-vinylpyrrolidone, N-octyl-pyrrolidone, N-cyclohexylpyrrolidone, N-dodecylpyrrolidone, N-isopropylpyrrolidone, N-hexylpyrrolidone, N-butylpyrrolidone, N-(2-hydroxyethyl)pyrrolidone, N-(2-aminoethyl)pyrrolidone, N-(3-trifluoromethylphenyl)-pyrrolidone, N-phenylpyrrolidone, N-benzylpyrrolidone, etc; N-methylpiperidone, N-ethylpiperidone, N-isopropylpiperidone, N-cyclohexylpiperidone, N-phenylpiperidone, etc.; N-methylcaprolactam, N-methylsuccinimide, N-methylmaleimide, N-methylglutaramide, etc.; 1,1,2,2-tetramethylurea; etc.

The process of the present invention allows another great drawback to be eliminated as it also enables any possible strong acid sites to be neutralized, due to cations such as $Al^{(III)}$ and $Fe^{(III)}$ englobed in the catalyst during the forming process or deriving from raw materials used in the synthesis or from other sources of pollution.

From a procedural point of view, thanks to the properties of the amide derivatives having general formula (I), the treatment of the catalyst can be carried out beforehand, i.e. before the reaction, or in continuous, during the reaction itself.

In the former case, the treatment can be carried out in the same epoxidation reactor, before the reaction, by conditioning the catalyst maintained in suspension in the solvent used (reaction foot) with a quantity of amide derivative dissolved in the solvent, which can vary from 0.01 to 0.5 grams per gram of catalyst, preferably from 0.02 to 0.25 grams, with treatment times generally ranging from 5 to 100 minutes, preferably from 15 to 30 minutes, and with temperatures varying from 0 to 100° C, preferably between 20 and 60° C. After the treatment, the reagents can be fed directly for epoxidation.

In the case of treatment in continuous, it is possible to add the desired amide derivative with one of the reagent streams fed to the reactor, in a quantity varying according to the reaction medium, temperature and olefin to be epoxidated. The high selectivity to epoxide obtained in this way can therefore be advantageously maintained for the entire reaction period.

The quantity of amide derivatives which can be usefully adopted in neutralizing the catalyst in continuous is maintained at 0.001 to 0.05 grams per gram of catalyst.

If a previously treated catalyst is used in the epoxidation reaction, it may be convenient, after a certain time, to integrate the amide compound with a suitable quantity dissolved in the feeding to the synthesis reactor. This quantity is generally quite small and is between 0.0001 and 0.005 grams per gram of catalyst.

Particularly with the last procedure described, it is possible to guarantee and maintain very high selectivities to epoxide from the very first reaction phases, without causing undesired reductions in the reaction rate.

The catalyst which can be used in the process of the present invention is selected from those generally known under the name of titanium silicalites which correspond to general formula (II):

$$xTiO_2(1-x)SiO_2 \qquad (II)$$

wherein x is between 0.0001 and 0.4, preferably between 0.001 and 0.04. These materials are known in scientific literature and can be prepared according to the method described in U.S. Pat. No. 4,410,501 which also specifies their structural characteristics. Titanium silicalites can also be used, in which part of the titanium is substituted by other metals such as boron, aluminum, iron or gallium. These substituted titanium silicalites and their preparation methods are described in published European patent applications 226.257, 226.258 and 226.825.

The quantity of catalyst used in the process for the preparation of epoxides of the present invention is not critical and is selected, however, so as to allow the completion of the epoxidation reaction in as short a time as possible. The quantity of catalyst generally depends on the reaction temperature, reactivity and concentration of the olefins, concentration of hydrogen peroxide and type of solvent. For example, the quantity of catalyst can range from 0.1 to 30 g per mole of olefin.

The olefinic compounds which can be used in the process of the present invention can be selected from organic compounds having at least one double bond and can be aromatic, aliphatic, alkylaromatic, cyclic, branched or linear. They are preferably olefinic hydrocarbons having from 2 to 30 carbon atoms in the molecule and containing at least one double bond.

Examples of olefins suitable for the purposes of the present invention are selected from those having general formula (III):

wherein: $R_4$, $R_5$, $R_6$, $R_7$, the same or different, can be H, an alkyl radical with from 1 to 20 carbon atoms, an aryl, alkylaryl radical with from 6 to 20 carbon atoms, a cycloalkyl radical with from 6 to 10 carbon atoms, an alkylcycloalkyl radical with from 7 to 20 carbon atoms the radicals $R_4$, $R_5$, $R_6$ and $R_7$, may form, as couples, saturated or unsaturated rings. In addition these radicals may contain halogen atoms, nitro, nitrile, sulfonic groups and relative esters, carbonyl, hydroxyl, carboxyl, thiol, amine and ether groups.

Examples of olefins which can be epoxidated with the process of the present invention are: ethylene, propylene, allyl chloride, allyl alcohol, butenes, pentenes, hexenes, heptenes, octene-1, 1-tridecene, mesityl oxide, isoprene, cyclo-octene, cyclohexene or bicyclic compounds such as norbornenes, pinenes, etc. The olefins can carry the above substituents both on unsaturated carbon atoms and in different positions.

The oxidating agent used in the process of the present invention is hydrogen peroxide ($H_2O_2$) or a compound which under the epoxidation conditions is capable of generating $H_2O_2$. The quantity of hydrogen peroxide with respect to the olefin is not critical but a molar ratio olefin/$H_2O_2$ ranging from 0.9 to 5, preferably between 0.95 and 3, is preferably used.

The epoxidation reaction can be carried out in one or more solvents liquid at the epoxidation temperatures. Solvents of a polar nature are typically used, such as alcohols (methanol, ethanol, isopropyl alcohol, t-butyl alcohol, cyclohexanol), ketones (for example acetone, methylethylketone, acetophenone), ethers (tetrahydrofuran, butylether), aliphatic and aromatic hydrocarbons, halogenated hydrocarbons, esters, glycols with a number of carbon atoms less than or equal to 6, aliphatic or aromatic nitriles (for example acetonitrile and benzonitrile). Methanol is preferably used and among ketones, acetone.

The temperatures used in the process of the present invention generally range from 0 to 150° C., preferably between 20 and 100° C., more preferably between 30 and 80° C.

The operating pressures are those which allow the olefin to be maintained in liquid phase at the temperature selected for the reaction. The operating pressure is generally higher than atmospheric pressure when gaseous olefins are used.

The epoxidation process of the present invention an be carried out batchwise, in semicontinuous or, referably, in continuous.

Various types of reactor can be used in the process of the present invention. For example a fixed-bed reactor, slurry reactor or fluid-bed reactor. Depending on the type of reactor, the catalyst can be used in the form of microspheres, granules or pellets of various forms and shapes.

The process for the preparation of olefinic epoxides of the present invention can be effected with known methods. For example, all the reagents can be introduced into the reaction zone contemporaneously or in sequence. At the end of the epoxidation reaction the products can be separated and recovered from the reaction mixture using conventional techniques such as distillation, crystallization, liquid-liquid extraction, steam stripping, etc. The catalyst together with the non-reacted products (olefin and $H_2O_2$) can be recovered and reused in subsequent epoxidation steps.

The following examples provide a better illustration of the invention without limiting its scope.

The titanium silicalite used in the examples is prepared according to what is described in published European patent application 100.119. It is appropriately conserved in a dry or inert atmosphere. The quantity of total titanium measured according to the FRX technique is equal to 2.64% by weight, whereas that resulting from chemical analysis is 2.62%.

EXAMPLE 1 (Comparative)

1.67 g of titanium silicalite in a mixture consisting of 460 g of methanol and 23 g of water are suspended at room temperature in a 1 liter reactor equipped with a mechanical stirrer with a gaseous effect, a thermostatic system (internal coil immersed in the reaction solution and external circulation jacket).

After the time necessary for bringing the system to a temperature of 40° C. and a total propylene pressure of 2.2 atm, 29.55 g of $H_2O_2$ at 57.55% w/w are fed.

The epoxidation progression is followed by analyzing the residual hydrogen peroxide by means of cerimetry and HPLC.

The results are indicated in the table below.

EXAMPLE 2

An epoxidation reaction is carried out under the same experimental conditions described in example 1, using however 250 ppm of 1-methyl-2-pyrrolidone dissolved in the solvent before thermostat-regulating and pressurizing the synthesis reactor.

The results obtained are indicated in the table.

EXAMPLE 3

The same procedure is carried out as in example 2 using however 1000 ppm of 1-methyl-2-pyrrolidone. The results obtained are indicated in the table.

EXAMPLE 4

The same procedure is carried out as in example 2 using however 100 ppm of 1-octyl-2-pyrrolidone. The results obtained are indicated in the table.

EXAMPLE 5

The same procedure is carried out as in example 2 using however 250 ppm of N,N-dimethylformamide. The results obtained are indicated in the table.

EXAMPLE 6

The same procedure is carried out as in example 3 using however 1000 ppm of N,N-dimethylformamide. The results obtained are indicated in the table.

EXAMPLE 7

The same procedure is carried out as in example 2 using however 1000 ppm of 1-methyl-2-piperidone. The results obtained are indicated in the table.

EXAMPLE 8

The same procedure is carried out as in example 2 using however 1000 ppm of N,N-dimethylacetamide. The results obtained are indicated in the table.

TABLE

Selectivity to propylene oxide obtained with titanium silicalite treated with amide derivatives

| Example | Amide derivative | Concentration ppm | Selectivity to epoxide at $H_2O_2$ conversions of | | |
|---|---|---|---|---|---|
| | | | 50% | 70% | 90% |
| 1 (reference) | — | — | 91.3 | 84.7 | 71.0 |
| 2 | 1-methyl-2- | 250 | 93.0 | 88.0 | 83.7 |

TABLE-continued

Selectivity to propylene oxide obtained with titanium silicalite treated with amide derivatives

| Example | Amide derivative | Concentration ppm | Selectivity to epoxide at $H_2O_2$ conversions of | | |
|---|---|---|---|---|---|
| | | | 50% | 70% | 90% |
| | pyrrolidone | | | | |
| 3 | 1-methyl-2-pyrrolidone | 1000 | 93.3 | 92.3 | 90.4 |
| 4 | 1-octyl-2-pyrrolidone | 100 | 93.6 | 90.5 | 87.2 |
| 5 | N,N-dimethylformamide | 250 | 93.1 | 88.4 | 84.1 |
| 6 | N,N-dimethylformamide | 1000 | 93.5 | 92.0 | 91.0 |
| 7 | 1-methyl-2-piperidone | 1000 | 93.9 | 89.2 | 87.0 |
| 8 | N,N-dimethylacetamide | 1000 | 92.7 | 88.4 | 86.3 |

We claim:

1. A process for the production of an epoxide, comprising reacting at least one olefin and hydrogen peroxide, in the presence of a catalyst consisting of titanium silicalite subjected to treatment with an organic molecule comprising an amide group substituted on the nitrogen atom having the general formula:

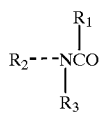

(I)

wherein:

$R^1$ is a hydrogen atom or an alkyl radical with from 1 to 20 carbon atoms, an aryl or alkylaryl radical, with from 6 to 20 carbon atoms, a cycloalkyl radical with from 7 to 20 carbon atoms, a heterocyclic radical with one or more heteroatoms, the same or different, selected from the group consisting of N, O and S;

$R_2$ and $R_3$, the same or different, are alkyl radicals with from 1 to 20 carbon atoms, aryl or alkylaryl radicals, with from 6 to 20 carbon atoms, cycloalkyl radicals with from 7 to 20 carbon atoms, heterocyclic radicals with one or more heteroatoms, the same or different, selected from the group consisting of N, O and S;

or the radicals $R^1$, $R_2$ and $R_3$, may form saturated or unsaturated rings in couples, and contain halogen atoms, nitro, nitrite, sulfuric groups, and relative esters, phosphoric groups, and relative esters, carbonyl, hydroxyl, carboxyl, thiol, amine and ether groups.

2. The process according to claim 1, wherein the treatment of the catalyst is previously carried out before the epoxidation reaction or in continuous during the reaction itself.

3. The process according to claim 1, wherein the catalyst is previously treated with a quantity of amide derivative (I) ranging from 0.01 to 0.5 grams per gram of catalyst.

4. The process according to claim 1, wherein the catalyst is treated continuously by adding the amide derivative (I) with one of the reagent streams fed to the reactor in a quantity ranging from 0.001 to 0.05 grams per gram of catalyst.

5. The process according to claim 1, wherein the titanium silicalites are selected from those having general formula:

$$x\mathrm{TiO}_2(1-x)\mathrm{SiO}_2 \qquad (II)$$

wherein x is between 0.0001 and 0.4.

6. The process according to claim 5, wherein part of the titanium of the catalyst is substituted by other metals such as boron, aluminum, iron or gallium.

7. The process according to claim 1, wherein the catalyst is used in a quantity ranging from 0.1 to 30 g per mole of olefin.

8. The process according to claim 1, wherein the olefin is selected from olefinic hydrocarbons having from 2 to 30 carbon atoms in the molecule and containing at least one double bond.

9. The process according to claim 1, wherein the hydrogen peroxide is used with a molar ratio olefin/$H_2O_2$ ranging from 0.9 to 5.

10. The process according to claim 1, wherein the epoxidation reaction is carried out in one or more solvents liquid at the epoxidation temperature.

11. The process according to claim 1, wherein the epoxidation temperatures range from 0 to 150° C.

* * * * *